(12) United States Patent
Frerichs

(10) Patent No.: US 7,326,974 B2
(45) Date of Patent: *Feb. 5, 2008

(54) SENSOR FOR MEASURING A GAS CONCENTRATION OR ION CONCENTRATION

(75) Inventor: Heinz-Peter Frerichs, St. Peter (DE)

(73) Assignee: Micronas GmbH, Freiburg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/719,648

(22) Filed: Nov. 21, 2003

(65) Prior Publication Data

US 2005/0146007 A1 Jul. 7, 2005

(30) Foreign Application Priority Data

Nov. 22, 2002 (DE) ................................ 102 54 523

(51) Int. Cl.
*H01L 23/58* (2006.01)
(52) U.S. Cl. ...................... 257/253; 257/108; 257/127; 257/418; 257/E21.064
(58) Field of Classification Search ................ 257/488, 257/489, 252, 253, 60, 127, 108, 418, E21.064
See application file for complete search history.

(56) References Cited

U.S. PATENT DOCUMENTS 4,385,274 A 5/1983 Shimada et al. ........... 324/71.6

(Continued)

FOREIGN PATENT DOCUMENTS

DE 3144459 10/1982

(Continued)

OTHER PUBLICATIONS

Paris, R.; Pawel, S.; Herzer, R.; Doll, T.; Kornetzky, P.; Gupta, R.P.; Eranna, G.;Low drift air-gap CMOS-FET gas sensor; Sensors, 2002. Proceedings of IEEE; vol. 1, Jun. 12-14, 2002 pp. 421-425.*

(Continued)

*Primary Examiner*—Howard Weiss
*Assistant Examiner*—John Ingham
(74) *Attorney, Agent, or Firm*—O'Shea, Getz & Kosakowski, P.C.

(57) ABSTRACT

A field-effect transistor used as a sensor for measuring a gas or ion concentration utilizes a surface structure such as rings along with surface profiling, for example elevations of the rings and depressions therebetween, to decrease the surface conductivity between a guard ring and the FET, to thereby increase the concentration rise per unit time of a gas signal and increase the time for a potential on a channel region of the FET to approximate the potential on a guard ring. The rings, which may be arranged around the FET structure, may be defined by a surface material different from the remaining surface material and thus having different surface conductivities. The surface profiling, together with the rings, can be utilized to increase an amount of time that may describe the equalization of the channel region potential to the guard ring potential. The elevations may have a surface conductivity different from, for example smaller than, that of the depressions. The surface profiling may be formed by forming the elevations on a thick oxide layer and spaced a distance apart. The annular structures arranged on the thick oxide layer and defined by a surface material different from the remaining surface material may have different surface conductivities and thus may form different, for example higher, contact resistances.

20 Claims, 2 Drawing Sheets

U.S. PATENT DOCUMENTS

| | | | |
|---|---|---|---|
| 4,411,741 A | 10/1983 | Janata | 204/1 |
| 4,764,797 A | 8/1988 | Shaw et al. | 257/253 |
| 5,911,873 A | 6/1999 | McCarron et al. | 205/789 |
| 6,525,390 B2 * | 2/2003 | Tada et al. | 257/489 |
| 6,929,728 B2 * | 8/2005 | Frerichs | 204/416 |
| 2002/0157950 A1 * | 10/2002 | Frerichs | 204/416 |

FOREIGN PATENT DOCUMENTS

| | | |
|---|---|---|
| DE | 4239319 | 4/1993 |
| DE | 4333875 | 4/1995 |
| DE | 19849932 | 5/2000 |
| EP | 0155726 | 9/1985 |
| EP | 0947829 | 10/1999 |

OTHER PUBLICATIONS

Gergintschew et al., "The capacitively controlled field effect transistor (CCFED) as a new low power gas sensor", Elsevier Science S.A., B 35-36, 1996, 285-289.

* cited by examiner

SENSOR FOR MEASURING A GAS CONCENTRATION OR ION CONCENTRATION

PRIORITY INFORMATION

This application claims priority from German application 102 54 523.5, filed Nov. 22, 2002.

BACKGROUND OF THE INVENTION

This invention relates in general to sensors and in particular to a sensor for measuring a gas or ion concentration.

Sensors with field-effect transistors (FETs) for measuring gas concentrations, where the gate of the FET may be a gas-sensitive layer whose work function depends on an ambient gas concentration, are known for example from U.S. Pat. No. 4,411,741.

Sensors with FETs for measuring ion concentrations, where the gate of the FET may be an ion-sensitive layer whose potential depends on the ionic concentration of an ambient liquid or gas, are known for example from U.S. Pat. No. 5,911,873.

Such sensors may generally be fabricated by counter-doping a semiconductor substrate to form therein a drain and a source and growing or depositing an insulating layer on the substrate between the source and the drain. An ion-sensitive layer can be applied directly onto the insulating layer. A gas-sensitive layer can be made a certain distance away, this configuration being known as a suspended-gate FET (SG-FET). Alternatively, a gate can be applied to the insulator and controlled capacitively by a gas-sensitive gate formed a certain distance away. Such a sensor, known as a capacitively controlled FET (CCFET), is described for example in German Patent DE 43 33 875 C2.

A disadvantage of these configurations may be that after a certain time, surface conductivity may pull a potential of the FET to a potential that is present on the gas-sensitive gate, causing the drain-source current to drift. To prevent this, a conductive ring, or guard ring, which can be set to a predetermined potential, may be laid around the FET. As such, the channel region of the FET may assume the potential of the guard ring after a certain time because of the surface conductivity of the region between the guard ring and the channel region. The distance between the guard ring and the channel region of the FET and the conductivity of the surface may define the time required for the channel region to take on the guard ring potential, thus establishing a relatively small concentration change per unit time that a gas signal for detection may have to be registered. This distance governs the size and the manufacturing costs of such a sensor.

What is needed is a sensor that can be manufactured at low cost, has relatively small dimensions, and achieves a relatively high degree of accuracy of measurement for a change in gas or ion concentration as a function of time, and in particular where the surface resistance between the guard ring and the FET may be made higher, so that the rise in concentration per unit time for a detectable gas signal may be increased.

SUMMARY OF THE INVENTION

A field-effect transistor used as a sensor for measuring a gas or ion concentration may allow for the surface conductivity between the guard ring and the FET to be decreased in a relatively simple way without any relatively large increase in the physical size of the circuit. Rings may be arranged around the FET structures, where the rings may be defined by a surface material different from the remaining surface material and thus having different surface conductivities and being able to form contact resistances. Surface profiling can also be provided to increase the RC time that may describe the equalization of the FET potential to the potential of the guard ring without impairing the functionality of the sensor configuration by the surface profiling. Such surface profiling may additionally further lengthen the RC time. Through use of surface profiling, the raised regions may have a surface conductivity different from, for example smaller than, the lowered regions.

The surface profiling may be formed in a simple manner by forming, on a previously generated thick oxide layer, elevations spaced a distance apart.

The annular structures arranged on the thick oxide layer and defined by a surface material different from the remaining surface material may have different surface conductivities and thus may form different, for example higher, contact resistances. The overall effect may be to increase the surface resistance between the guard ring and the FET so that the concentration rise per unit time of a gas signal may be increased.

These and other objects, features and advantages of the present invention will become more apparent in light of the following detailed description of preferred embodiments thereof, as illustrated in the accompanying drawings.

DETAILED DESCRIPTION OF THE INVENTION

Figure 1:
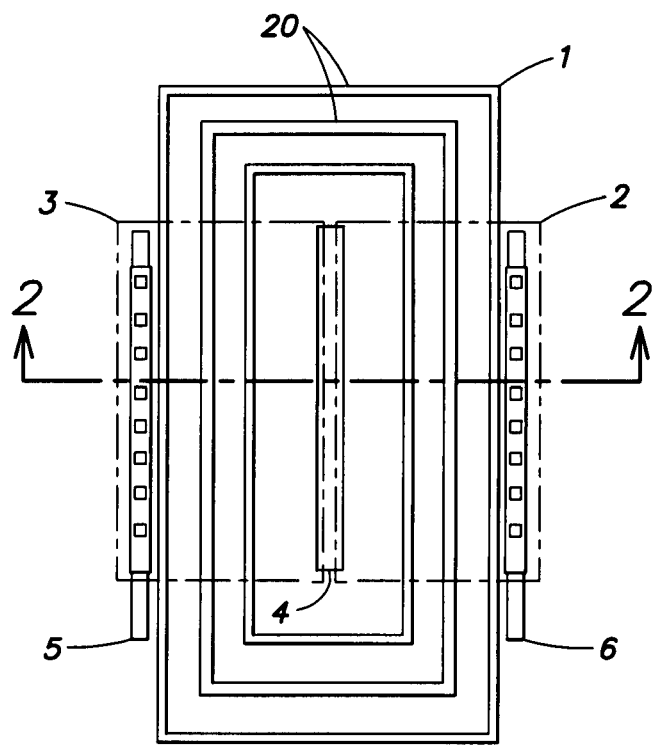
FIG. 1 is a top view of an embodiment of a sensor for measuring a gas or ion concentration.
Figure 2:
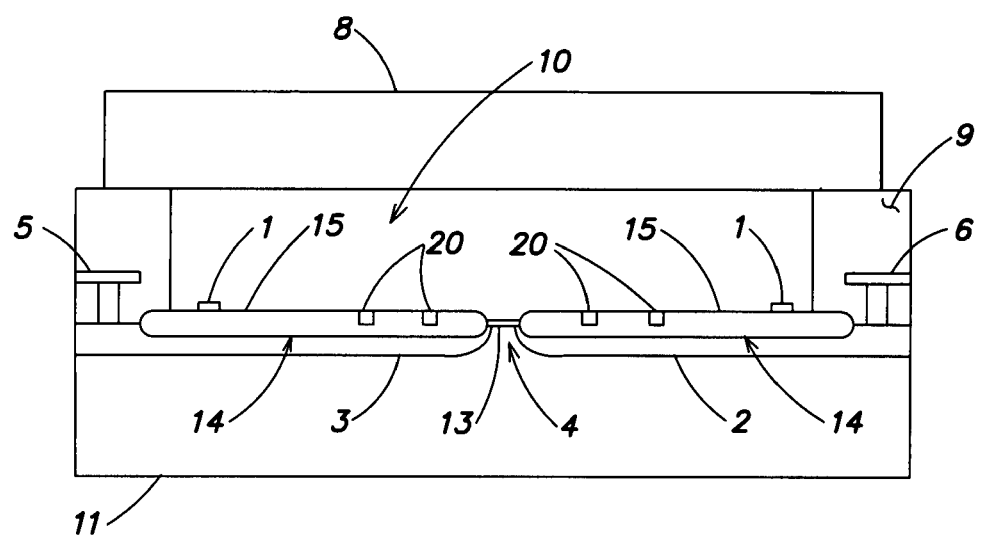
FIG. 2 is a section along line 2-2 in FIG. 1.

Referring to FIGS. 1 and 2, on a substrate 11 of a first charge-carrier type, for example n-doped silicon, a gas sensor may have a source 2 and a drain 3 of a second charge-carrier type, for example p-doped silicon, which may be formed, for example, by ion implantation. The source 2 may have a source terminal 6 and the drain 3 may have a drain terminal 5. In the substrate 11 between the source 2 and the drain 3 there may be a channel region 4 on which a thin oxide layer 13 may be formed. Insulator layers 14, for example thick oxide layers 14, may be formed on the source 2 and the drain 3. A guard ring 1 made of a conductive material may be applied onto the surfaces of the source 2 and the drain 3. The guard ring 1 may encircle the channel region 4 and can be set to a predetermined potential.

Arranged on lateral insulator regions 9 may be a gas-sensitive gate layer 8 whose potential depends on an ambient gas concentration. An air gap 10 may be formed between the gate layer 8 and the thin oxide layer 13. The thin oxide layer 13 can be for example 3-50 mm thick and may function, together with the air gap 10, as a gate dielectric. Changes in the concentration of the ambient gas can thus be detected as changes in the source-drain current of the FET.

Between the thin oxide layer 13 above the channel region 4 and the guard ring 1 there may be a surface structure by which the surface resistance between the guard ring 1 and the FET may be increased. Through suitable layer deposition steps and the use of photomasks as well as subsequent etching, materials, for example in the form of one or a plurality of ring structures 20, may be arranged on the thick oxide layer 14 or embedded partially or fully therein. The ring structures 20 can be formed for example as circular rings, quadrilaterals or polygons. Aluminum or aluminum with a copper content may be a suitable material for the ring structures 20, such that the ring structures 20 form an aluminum oxide on their surface upon exposure to ambient air. As such, the resistance on the surface between the guard ring 1 and the channel 4 may be increased, such that the RC time required for equalization of the FET potential to the guard ring potential may be prolonged.

Figure 3:
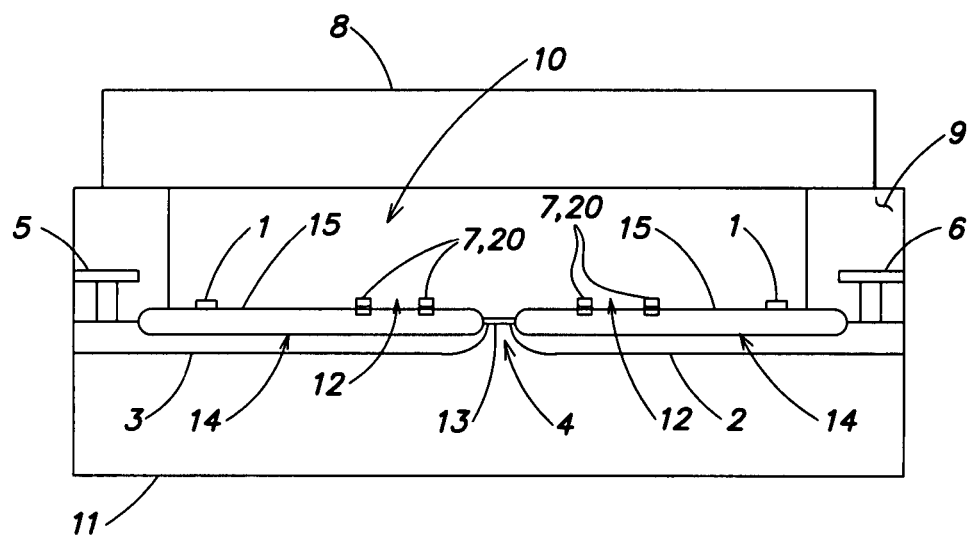
FIG. 3 is a section through an embodiment of a sensor.

FIG. 3 illustrates a sensor that is somewhat similar to the sensor of FIG. 2. In the sensor of FIG. 3, the ring structures 20 may rise as elevations 7 above the surface 15 of the thick oxide layer 14 toward the air gap 10. The regions 12 lying between the elevations 7 may be identified as depressions 12. The raised ring structures 20 may have a surface conductivity lower than that of the depressions 12. The process of forming the elevations 7 and the depressions 12 may lead to surface profiling of the thick oxide layer 14. The profiling of the surface 15 of the thick oxide layer 14 can be formed by the application of layers on the thick oxide layer 14 through appropriate deposition steps followed by etching steps defined by photomasks to uncover the depressions 12. The elevations 7 applied by deposition may be made of a material different from that of the thick oxide layer 14. A material with a low surface conductivity, such as aluminum or aluminum with a copper content, may be used for surface profiling. Upon contact with air, an aluminum oxide is formed on the surface, so that the surface conductivity may be lowered. The thick oxide layer 14 may be uncovered where the layers are etched in the depressions 12. The thin oxide layer 13 can also be implemented as a capacitance.

Figure 4:
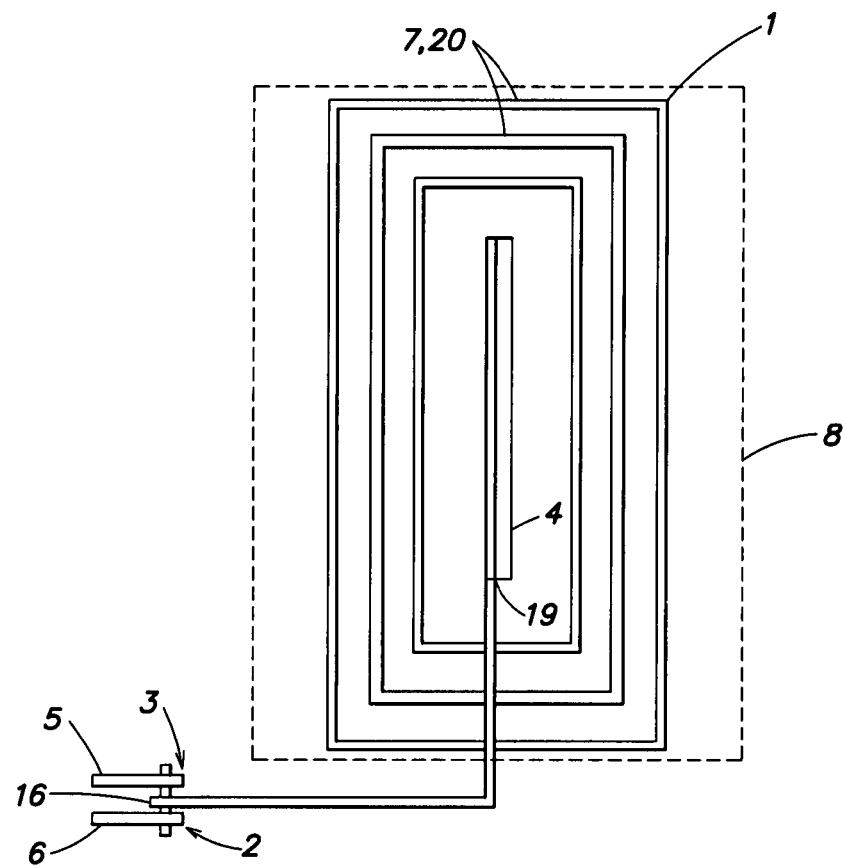
FIG. 4 is a top view of an embodiment of a sensor for measuring a gas or ion concentration.

Another embodiment of the sensor is illustrated in FIG. 4. Therein, the field-effect transistor formed from the source 2 and the drain 3 may be spatially separated from the air gap 10 between the gate layer 8 and the channel region 4. The gate 16 of the field-effect transistor may be led in an insulated manner via an electrode 19 below the elevations 7 into the channel region 4 below the air gap 10.

Although the present invention has been shown and described with respect to several preferred embodiments thereof, various changes, omissions and additions to the form and detail thereof, may be made therein, without departing from the spirit and scope of the invention.

What is claimed is:

1. A sensor for measuring a parameter, comprising:
   a substrate;
   a drain disposed on the substrate;
   a source disposed on the substrate;
   a channel region disposed between the drain and the source;
   a conductive guard ring disposed outside the channel region;
   a sensitive gate layer with a potential that depends on the parameter;
   an air gap disposed between the gate layer and the channel region; and
   an insulating layer disposed between the guard ring and the channel region, the insulating layer having a surface on a portion of which is disposed a ring structure having a surface conductivity different from a surface conductivity of a remaining portion of the surface of the insulating layer to thereby increase an amount of time in which the potential of the channel region equals the potential of the conductive guard ring.

2. The sensor of claim 1, further comprising surface profiling having at least one elevation and at least one depression and disposed between the guard ring and the channel region.

3. The sensor of claim 2, further comprising a second insulating layer disposed over the channel region.

4. The sensor of claim 2, where the ring structure comprises an insulating material disposed on the insulating layer.

5. The sensor of claim 2, where the ring structure comprises a concentric structure.

6. The sensor of claim 2, where the parameter comprises a gas concentration.

7. The sensor of claim 2, where the parameter comprises an ion concentration.

8. A sensor for measuring a concentration of an ambient parameter, comprising:
   a substrate;
   a channel region formed in the substrate;
   a conductive guard ring arranged outside the channel region;
   a sensitive gate layer whose potential depends on the concentration of the ambient parameter, an air gap disposed between the gate layer and the channel region;
   an oxide layer disposed between the guard ring and the channel region, a surface of the oxide layer having a ring structure arranged on a portion thereof, the ring structure having a surface conductivity different from a surface conductivity of a remainder of the surface; and
   a source and a drain forming a field-effect transistor, the transistor being spatially separated from the air gap between the gate layer and the channel region, the transistor having a gate that is connected by an electrode to the channel region, the different surface conductivities between the ring structure and the remainder of the surface increasing an amount of time in which the potential of the channel region equals the potential of the conductive guard ring.

9. The sensor of claim 8, where the ambient parameter comprises a gas.

10. The sensor of claim 8, further comprising surface profiling having at least one elevation and at least one depression and disposed between the guard ring and the channel region.

11. The sensor of claim 8, further comprising an insulating thin layer disposed over the channel region.

12. The sensor of claim 8, where the ring structure comprises an insulating material disposed on the oxide layer.

13. The sensor of claim 8, where the ring structure comprises a concentric structure.

14. The sensor of claim 8, where the ambient parameter comprises an ion concentration.

15. A sensor for measuring an ambient parameter, comprising:
   a source;
   a drain;
   a channel region between the source and the drain;
   a conductive guard ring outside the channel region;
   a gate layer with a potential that depends on the ambient parameter;
   an air gap between the gate layer and the channel region; and
   an insulating layer between the guard ring and the channel region, the insulating layer having a surface on a portion of which a ring structure is arranged having a surface conductivity different from a surface conductivity of a remaining portion of the surface of the insulating layer to thereby increase an amount of time in which the potential of the channel region equals the potential of the conductive guard ring.

16. The sensor of claim 15, further comprising at least one elevation and at least one depression formed with respect to the insulating layer and between the guard ring and the channel region.

17. The sensor of claim 15, where the ambient parameter comprises a gas concentration.

18. The sensor of claim 15, where the ambient parameter comprises an ion concentration.

19. The sensor of claim 15, where the insulating layer comprises an oxide layer.

20. The sensor of claim 15, further comprising an insulating thin layer over the channel region.

* * * * *